United States Patent [19]
Allen et al.

[11] Patent Number: 5,282,810
[45] Date of Patent: Feb. 1, 1994

[54] SURGICAL ANASTOMOSIS DEVICE

[75] Inventors: William J. Allen, Stratford; George Jessup, Brookfield; Lester F. Miller, Danbury; Milton W. Brumaghim, Newtown, all of Conn.

[73] Assignee: American Cyanamid Company, Wayne, N.J.

[21] Appl. No.: 865,236

[22] Filed: Apr. 8, 1992

[51] Int. Cl.⁵ .............................................. A61B 17/00
[52] U.S. Cl. .................................. 606/150; 606/151; 606/153; 606/154
[58] Field of Search ............... 606/151, 153, 154, 150, 606/148; 623/1, 12; 128/899

[56] References Cited

U.S. PATENT DOCUMENTS

| | | | |
|---|---|---|---|
| 2,638,901 | 5/1953 | Sugarbaker | 606/153 |
| 3,168,096 | 2/1965 | Brummelkamp | 606/153 |
| 3,297,033 | 1/1967 | Schmitt et al. | 128/335.5 |
| 3,771,526 | 11/1973 | Rudie | 128/334 C |
| 4,055,186 | 10/1977 | Leveen | 128/334 C |
| 4,154,241 | 5/1979 | Rudie | 128/334 C |
| 4,467,804 | 8/1984 | Hardy et al. | 128/334 C |
| 4,552,148 | 11/1985 | Hardy, Jr. et al. | 128/334 C |
| 4,567,891 | 2/1986 | Kanshin et al. | 606/153 |
| 4,576,167 | 3/1986 | Noiles | 128/334 R |
| 4,603,693 | 8/1986 | Conta et al. | 128/305 |
| 4,646,745 | 3/1987 | Noiles | 128/334 R |
| 4,667,673 | 5/1987 | Li | 128/334 C |
| 4,766,898 | 8/1988 | Hardy et al. | 128/334 C |
| 4,907,591 | 3/1990 | Vasconcellos et al. | 606/171 |
| 4,931,057 | 6/1990 | Cummings et al. | 606/153 |
| 4,957,499 | 9/1990 | Lipaton et al. | 606/153 |
| 4,964,863 | 10/1990 | Kanshin et al. | 128/898 |

FOREIGN PATENT DOCUMENTS

WO87/06448 11/1987 World Int. Prop. O. .......... 606/153

Primary Examiner—Stephen C. Pellegrino
Assistant Examiner—Jeffrey A. Schmidt
Attorney, Agent, or Firm—Charles F. Costello, Jr.

[57] ABSTRACT

A transanal insertion device for surgically inserting an anastomosis ring having two unitary members into a tubular anatomic member comprises a distal adapter, a proximal adapter and an actuator. The distal adapter includes a hollow distal sleeve and a spring-loaded distal spool axially movable within the distal sleeve. The distal spool is biased in a first direction by a distal spring and includes alignment fingers pivotably connected thereon for aligning a first unitary member. The proximal adapter has a hollow proximal sleeve and a spring-loaded proximal spool axially movable within the proximal sleeve. The proximal spool is biased in a second direction by a proximal spring and includes alignment fingers connected thereon for aligning a second unitary member. The proximal member also includes a proximal gripper for securing the second unitary member on the proximal hollow sleeve. The actuator includes an elongated tube with a collar connected to its distal end and a handle assembly connected to its proximal end. First and second flexible rods connected to the handle assembly extend through the elongated tube. The flexible rods are manipulated to engage the distal adapter and draw it relative to the proximal adapter. The rods are also manipulated to release the distal and proximal adapters from their respective unitary members so the distal adapter, the proximal adapter and the actuator can be withdrawn transanally.

56 Claims, 8 Drawing Sheets

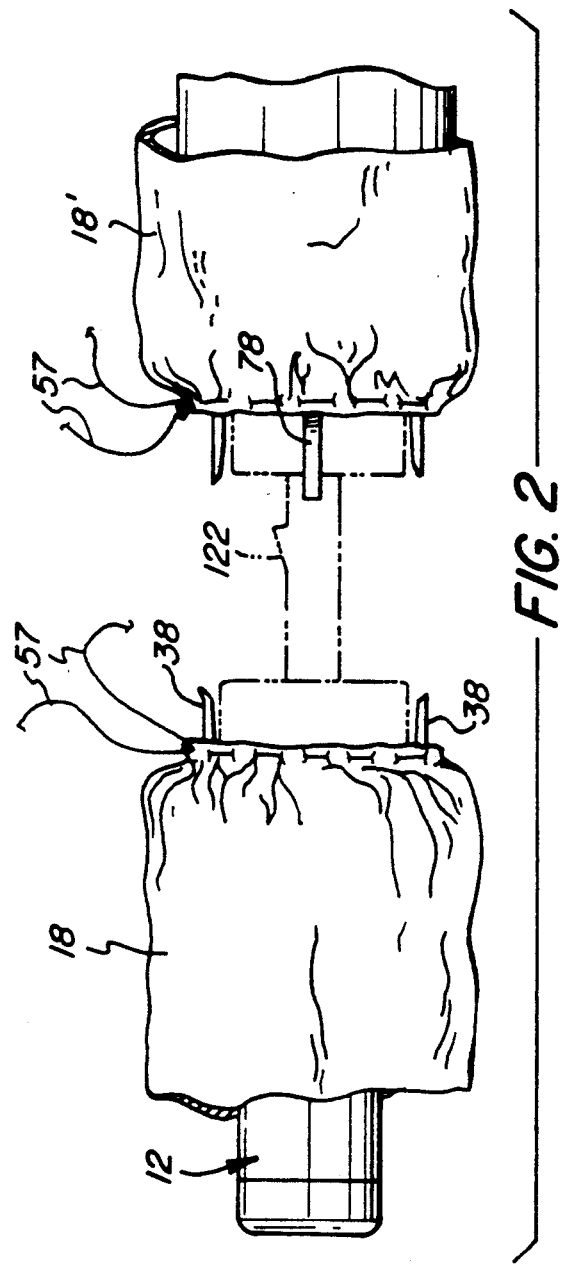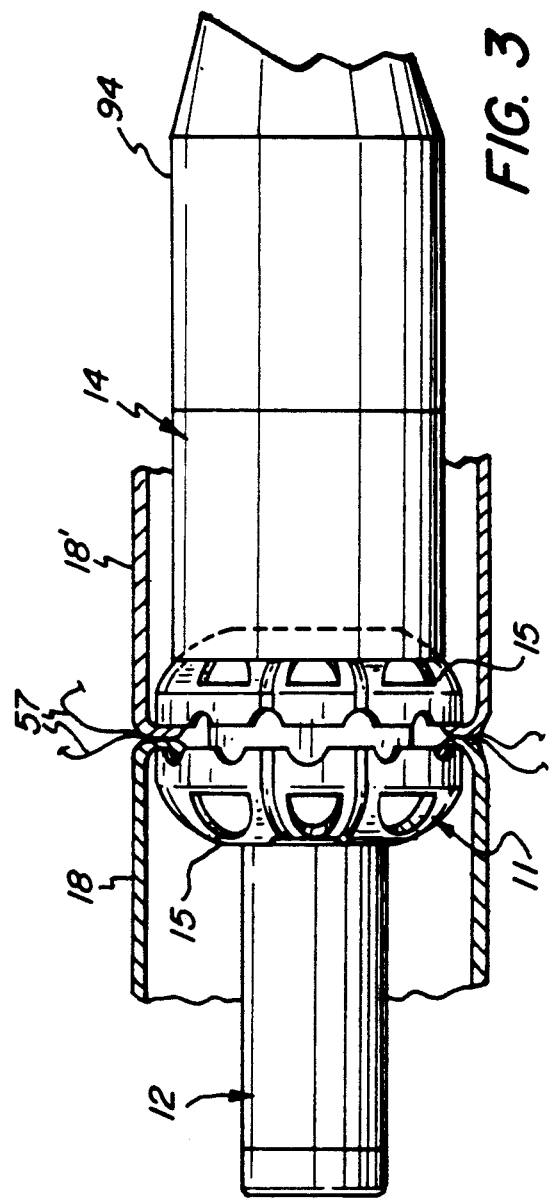

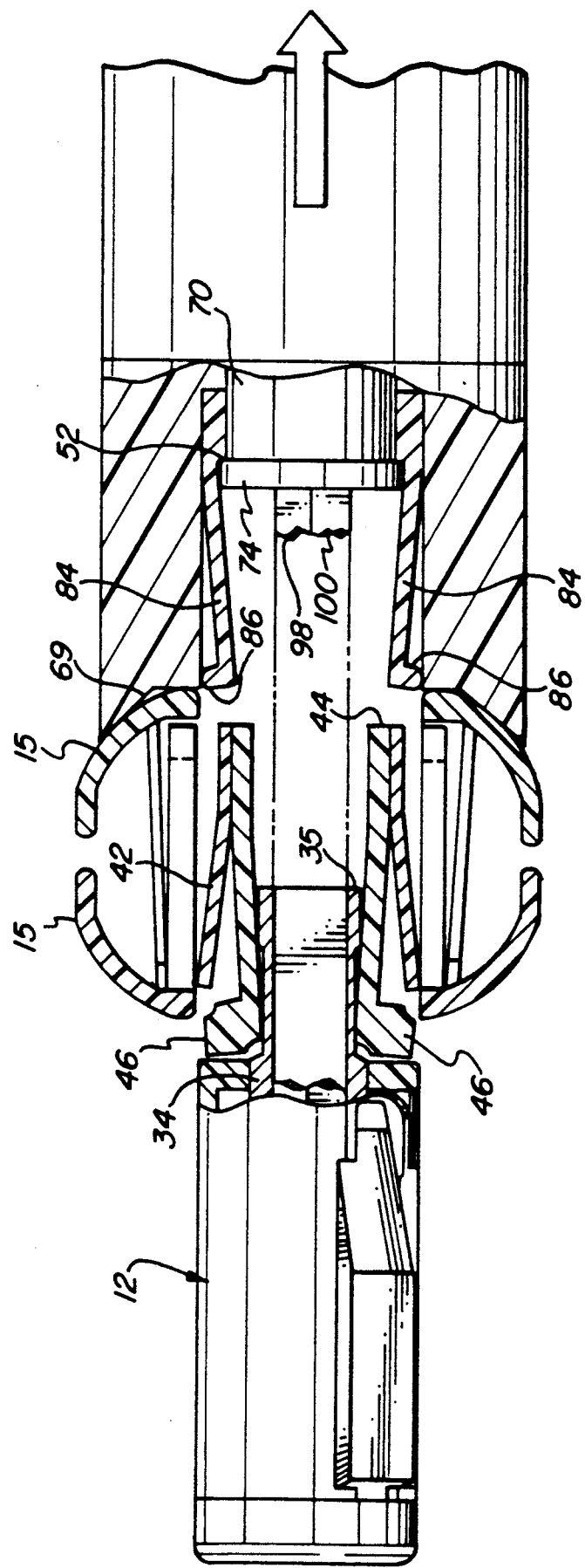

SURGICAL ANASTOMOSIS DEVICE

BACKGROUND OF THE INVENTION

1. Field of the Invention

This invention relates to a surgical device, and more particularly to an anastomosis ring insertion device for use in anastomosing tubular body organs in connection with, for example, intestinal surgery.

The subject invention is particularly useful for anastomosing the lower colon, or bowel section, of the intestines, and is inserted transanally through the patient.

After a surgical procedure such as cutting and removing a diseased or cancerous portion of the bowel, the severed ends of the bowel must be anastomosed. Several procedures are available for connecting together two sections of hollow tubular body organs such as the intestines. Known procedures include suturing, stapling or clamping the severed ends together. For example, U.S. Pat. Nos. 4,576,167, No. 4,603,693 and No. 4,646,745 are directed to circular surgical staplers for joining hollow body organs.

Another procedure using anastomosis buttons and clamps is disclosed in U.S. Pat. Nos. 3,771,526, No. 4,055,186 and No. 4,154,241. These devices may utilize inserter rods which are forced upwardly into the rectum through the anus to position one half of a clamp device in the lower colon and engage the other half of the clamp device positioned in the upper colon to draw the two halves together.

Still another procedure involves use of an anastomotic device that is the subject of U.S. Pat. Nos. 4,467,804, No. 4,552,148 and No. 4,766,898, which are assigned to the assignee of the present application, and marketed and sold under the VALTRAC® trademark. The anastomotic device receives the open ends of two tubular body organs to be anastomosed over a pair of ring members. The ring members have annular connecting means which mate with each other to clamp the body organs contiguous to each other so they can grow and heal together.

The anastomotic device, which will be referred to hereinafter and in its embodiment for use in the intestines as a bowel anastomosis ring, is pictured in FIGS. 12 through 14. A complete anastomosis ring 11 is shown in FIG. 12 and is comprised of two identical unitary members 13 of mushroom cap configuration. FIGS. 13 and 14 show a bottom plan view and top plan view, respectively, of the unitary member. The bottom plan view in FIG. 13 shows a ring member 15 having a pair of diametrically opposed depending legs 17 each supporting a plurality of engaging pawls 19. Alternately positioned between the depending legs and opposite to each other are depending engaging members 21, each of which has a pawl engaging recess 23 to cooperatively receive the pawls when the two unitary members 13 are joined together to form the anastomosis ring. For ease of reference, the ring member will be referred to as the head of the anastomosis ring and the depending legs and engaging members will be referred to as the neck.

FIG. 14 shows the top of the unitary member molded to form four notches 25 and four ridges 27 alternately positioned around its inner periphery.

As shown in FIG. 12, the pawls 19 are positioned on each depending leg 17 such that the unitary members can mate in an engaged position as shown in solid lines, or in a fully closed position as shown in solid and broken lines. A profile of the engaging pawl showing engaging edge 29 and slope 31 can also be seen in FIG. 12.

The unitary members 13 are formed of a bio-absorbable material that permits disintegration of the device in a relatively short period of time after healing of the tubular body organ ends begins. Acceptable materials for forming the anastomosis rings are disclosed in U.S. Pat. No. 3,297,033 and are referred to as poly-hydroxyacetic ester and lactide copolymers. Molded surgical articles made from a wide variety of glycolide/lactide copolymers are well known in the art.

2. Description of the Prior Art

U.S. Pat. No. 4,667,673, also assigned to the assignee of the present application, discloses an applicator device for mounting and inserting the bowel anastomosis ring described above and a method for using the applicator. The device includes a mounting extension for mounting the two halves of the bowel anastomosis ring and an inserter which may be curved. The inserter portion of the applicator passes through the interior of the rectum and out through the exterior of the anus so that the placement of the bowel anastomosis ring can be done without being exposed to the dirty and contaminated end of the bowel.

As a further improvement in an applicator device for inserting a bowel anastomosis ring, the present invention is directed to a transanal insertion device and provides further advantages for mounting and inserting the bowel anastomosis ring within, for example, the intestines.

SUMMARY OF THE INVENTION

It is a principal object of the present invention to improve upon and enhance an applicator insertion device for surgically inserting an anastomosis ring.

Accordingly, it is an object of the invention to provide an insertion device for surgically inserting a unitary member of an anastomosis ring in an open end of the lower bowel through the anal orifice.

It is a further object of the invention to provide an insertion device for inserting a unitary member of the anastomosis ring in an open end of the upper bowel through an abdominal insertion.

It is still a further object of the invention to provide an insertion device that swiftly and easily mates the unitary members of the anastomosis ring to clamp the open ends of the bowel in a contiguous manner.

It is still a further object of the invention to provide an insertion device that releases mounting adapters from the unitary members and withdraws the adapters through the anal orifice.

These and other objects are achieved by the transanal anastomosis ring insertion device of the present invention, which in a preferred embodiment comprises distal adapter means for temporarily mounting a first unitary member secured within an upper open end of the anatomic member, and proximal adapter means for temporarily mounting a second unitary member secured within a lower open end of the anatomic member. Actuating means, connected to the proximal adapter means, engages the distal adapter means and draws it relative to the proximal adapter mean to interlock the unitary members and releases the distal adapter means and the proximal adapter means from their respective unitary members.

In another preferred embodiment, a surgical applicator for inserting an anastomosis ring having first and second unitary members into a tubular anatomic member comprises distal applicator means for positioning a first unitary member in an upper open end of a tubular anatomic member, with a distal applicator means having a distal adapter for securing the first unitary member and a distal adapter holder for inserting the distal adapter and the first unitary member into the upper open end. A proximal applicator means positions a second unitary member in a lower open end of the tubular anatomic member and includes a proximal adapter for securing the second unitary member and actuating means for engaging the distal adapter and drawing it relative to the proximal adapter to interlock the unitary members and for releasing the distal adapter and the proximal adapter from their respective unitary members.

In another preferred embodiment, a transanal insertion device for surgically inserting a anastomosis ring having two unitary members into a tubular anatomic member comprises a distal adapter having a hollow distal sleeve, a spring-loaded distal spool axially movable within the distal sleeve, a distal spring for biasing the distal spool in a first direction and alignment fingers pivotally connected to the distal spool for aligning a first unitary member. The distal adapter also includes a distal gripper and a retaining sleeve for securing the first unitary member on the hollow distal sleeve. A proximal adapter has a hollow proximal sleeve and a spring-loaded proximal spool axially movable within the proximal sleeve. The proximal spool is biased in a second direction by a proximal spring and includes alignment fingers connected thereon for aligning the second unitary member. The proximal adapter also includes a proximal gripper for securing the second unitary member on the proximal hollow sleeve. An actuator includes an elongated tube with a collar connected to its distal end and a handle assembly connected to its proximal ends. First and second flexible rods are connected to the handle assembly and extend through the elongated tube.

In yet another preferred embodiment the present invention is a method for surgically anastomosing a tubular anatomic member with an anastomosing ring having two mating unitary members and utilizing a distal adapter for mounting one of the unitary members, a proximal adapter for mounting the other unitary member and an actuator for mating the unitary members. The method comprises the steps of inserting the distal adapter and the unitary member through a bodily incision into an open end of an upper tubular member, transanally inserting the actuator connected to the proximal adapter and unitary member into an open end of a lower tubular member, engaging the distal adapter with the actuator, drawing the distal adapter and proximal adapter together with the actuator to mate the unitary members, releasing the distal adapter from the one unitary member and releasing the proximal adapter from the other unitary member, and withdrawing the distal adapter, the proximal adapter and the actuator from the anatomic member transanally.

These and other objects, aspects, features and advantages of the present invention will become apparent from the following detailed description of the preferred embodiment taken in conjunction with the drawings.

BRIEF DESCRIPTION OF THE DRAWINGS

FIG. 2 is a partial side elevational view of the open ends of the upper and lower bowels purse-string-sutured around distal and proximal adapters in accordance with the present invention;

FIG. 3 is a partial cross.sectional view of a closed anastomosis ring showing the open ends of the upper and lower bowels clamped therebetween in accordance with the present invention;

FIG. 6 is a side elevational view, partly in cross-section, showing the distal and proximal adapters being readied to be withdrawn from the closed anastomosis ring in accordan-ce with the present invention;

DESCRIPTION OF THE PREFERRED EMBODIMENTS

For convenience of reference, as used herein, the term "distal" will refer to that part of the device which is furthest away from the surgeon.user, and the term "proximal" refers to that part of the device which is closest to the surgeon-user.

Figure 1:
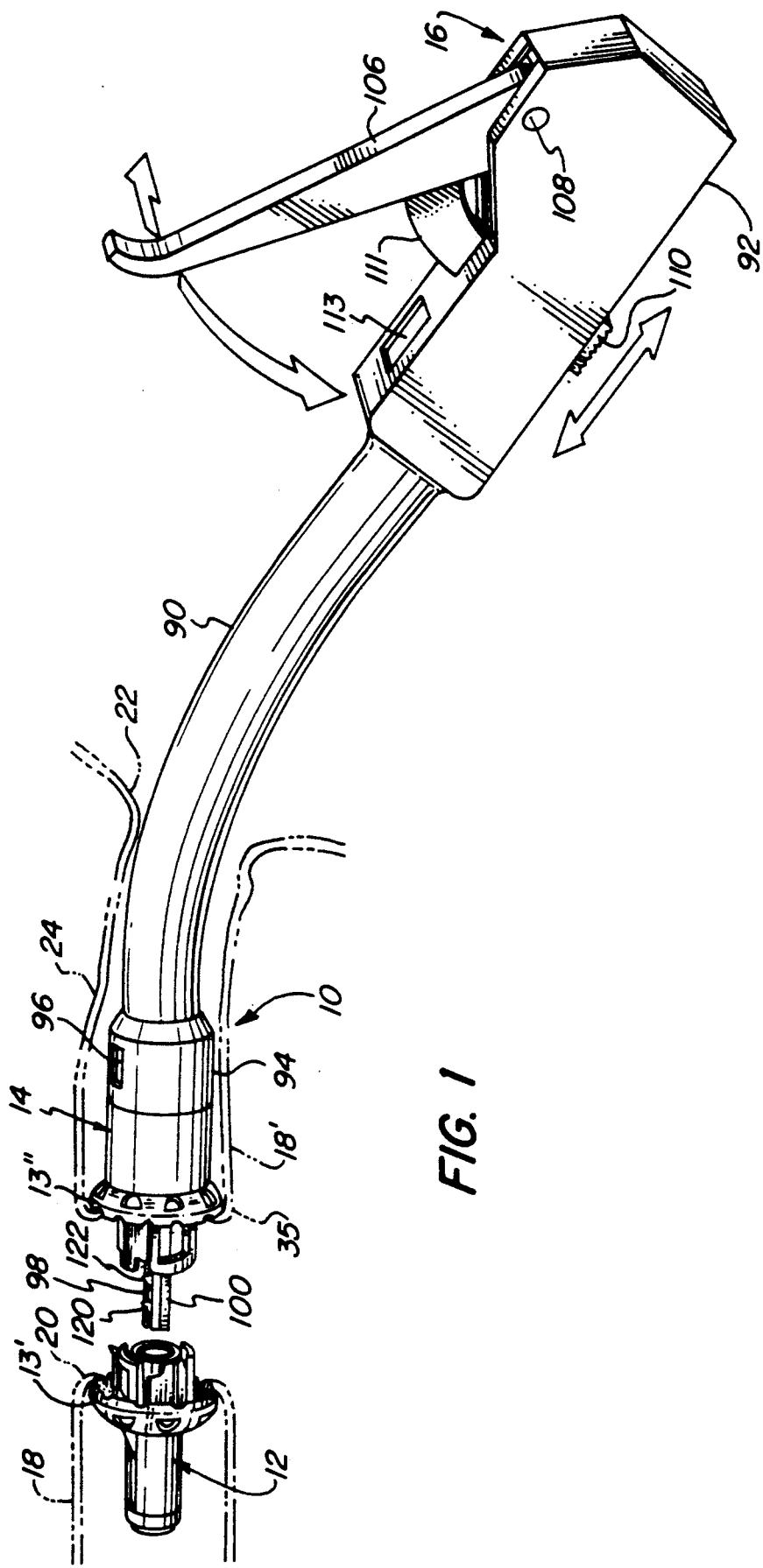
FIG. 1 is a perspective view of the transanal anastomosis ring insertion device in accordance with the present invention.

Referring initially to FIG. 1, the three main components of the anastomosis ring insertion device 10 are shown as distal adapter 12, proximal adapter 14 and actuator 16. The distal adapter secures thereon distal unitary member 13' and the proximal adapter secures thereon proximal unitary member 13".

Generally speaking, and in a manner which will be described in greater detail below, the distal adapter shown in FIG. 1 is positioned within an open end 20 of upper bowel 18 and the actuator with the proximal adapter connected thereto enters the patient through anal orifice 22 and is guided through the rectum 24 to position the proximal unitary member 13" in an open end 35 of lower bowel 18'. The open ends of the upper and lower bowels are snugly tightened around their respective unitary members by means of a purse-string suture, and then rods 98 and 100 of the actuator are manipulated to close the unitary members to form the anastomosis ring and clamp the open ends of the upper and lower bowel together. The actuator is further manipulated to release the anastomosis ring from the distal and proximal adapters and then the actuator, with the distal and proximal adapters, is withdrawn through the anal orifice. This leaves the anastomosis ring within the body to anastomose the open ends of the bowel.

Figure 4:
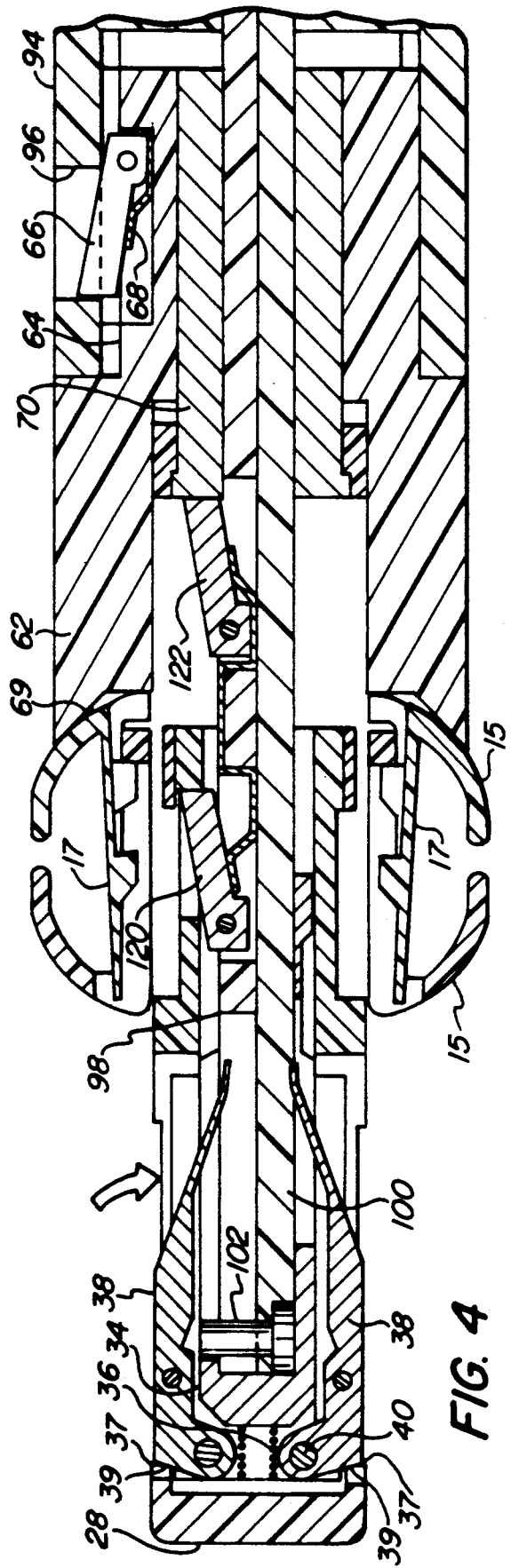
FIGS. 4 and 5 are cross-sectional views of the distal and proximal adapters being readied to be withdrawn from a closed anastomosis ring in accordance with the present invention.

The distal adapter 12 will be discussed in detail with primary reference to FIGS. 7, 9 and 10. As shown in these figures, the distal adapter comprises a plastic distal sleeve 26 with a main diameter section 30 and a reduced diameter section 32. The reduced diameter section includes an engaging opening 33 for purposes which will be explained below. A plastic cap 28 fits on one end of the sleeve while the other end is open and receives therein a spring-loaded tubular distal spool 34 made of, for example, stainless steel. A distal spring 36 biases the tubular spool in a proximal, or first, direction toward the open end of the sleeve. The first direction is represented by arrowhead A in FIG. 9 and a second direction is represented by arrowhead B. The tubular spool includes two diametrically opposed distal alignment fingers 38 pivotably disposed on the spool by pivot pins 40. The alignment fingers, which are also preferably made of stainless steel, extend through elongated slots 35 in the plastic sleeve so they can move axially with the tubular spool. When the tubular spool is fully compressed against the spring 36 as shown in FIG. 4, cam surfaces 37 on the sleeve contact cam surfaces 39 at the base of the alignment fingers to bias the alignment fingers radially inwardly.

Figure 9:
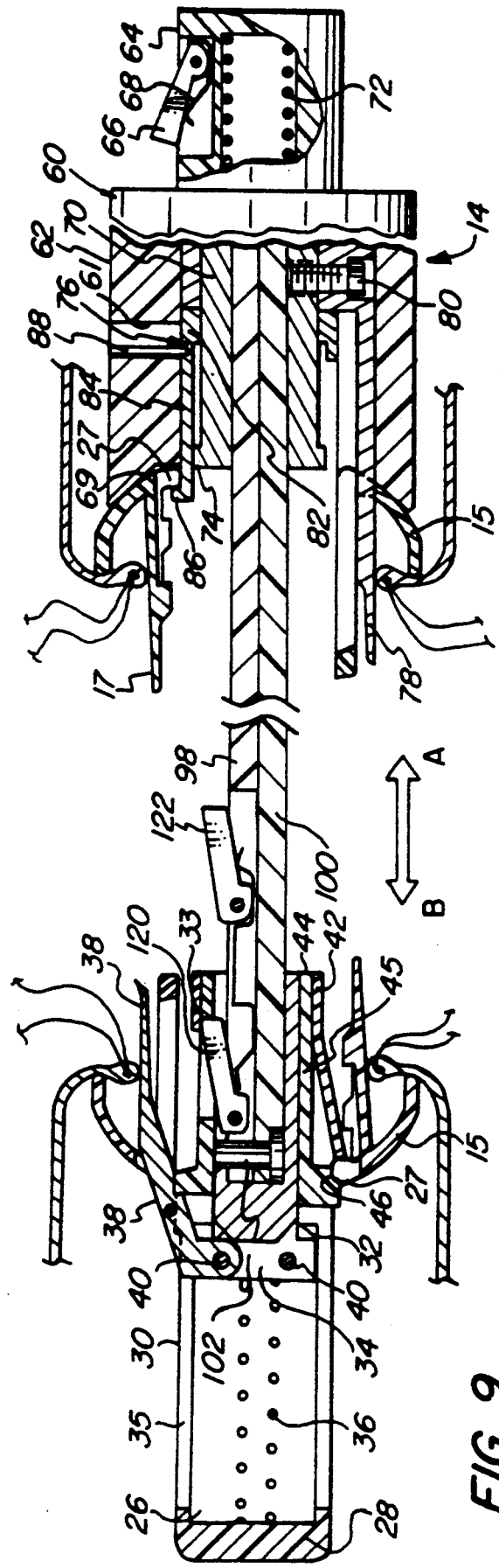
FIG. 9 is a cross-sectional view showing an applicator extending through the proximal adapter and engaged with the distal adapter in accordance with the present invention.
Figure 10:
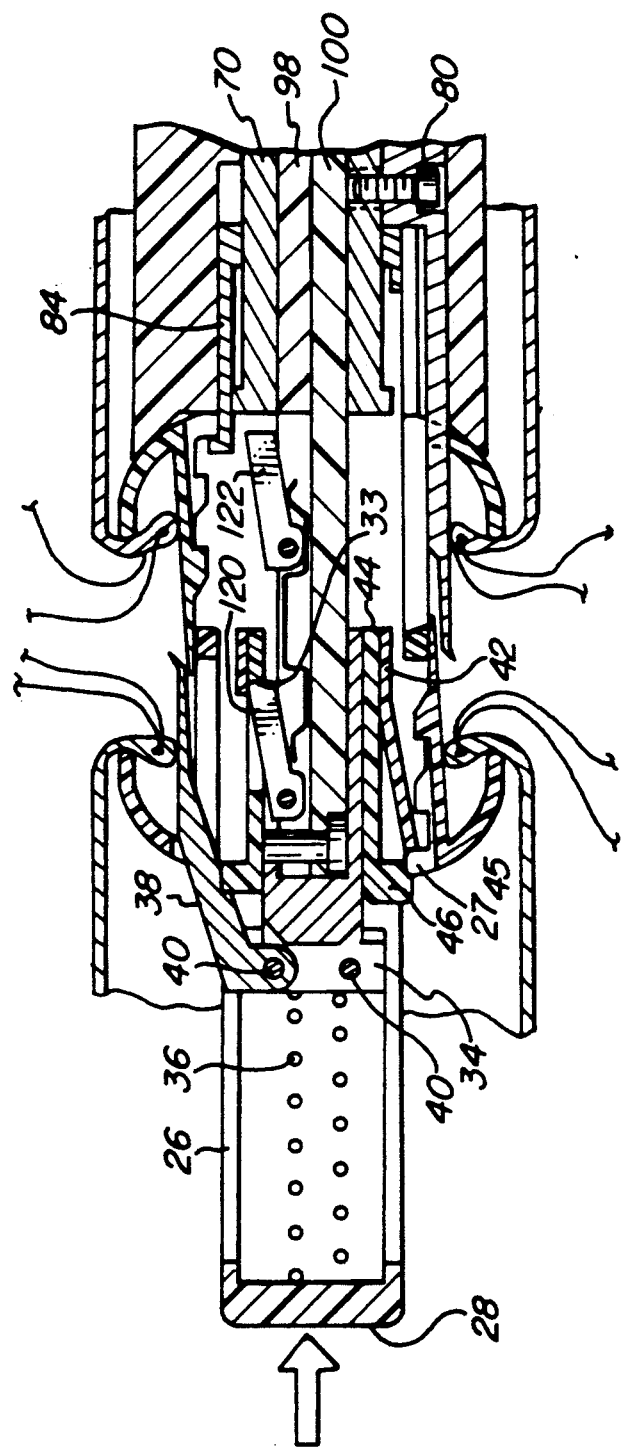
FIG. 10 is a cross-sectional view showing the distal adapter and proximal adapter being drawn together by the applicator in accordance with the present invention.

With reference to FIGS. 9 and 10, a four-fingered tubular gripper 42 and a retaining sleeve 44 are coaxially secured on the reduced diameter section 32 of the plastic sleeve. The retaining sleeve includes four radially-spaced fingers 45 each having a projection 46 and cooperates with the four-fingered tubular gripper to mount the unitary member onto the distal adapter.

The unitary member is mounted on the distal adapter by sliding it over the open end of the plastic sleeve so that the alignment fingers 38 on the tubular spool enter two diametrically opposed notches 25 in the unitary member. As the unitary member slides over the plastic sleeve, the ridges 27 depress the four-fingered tubular gripper radially inwardly until the head of the unitary member passes over the gripper. At this point, the four-fingers flex radially outwardly to contact an underside of the ridges and prevent the unitary member from moving toward the open end of the sleeve. At the same time, the ridges come to rest against the projections on the retaining sleeve and thus are prohibited from moving any further toward the cap end 28 as shown in FIG. 9. The fingers 45 on the retaining sleeve are aligned with openings (unshown) in the reduced diameter section of the plastic sleeve. However, the tubular spool prevents the fingers from moving radially inwardly when it is biased in its rest position by the spring 36, also as shown in FIG. 9.

Figure 7:
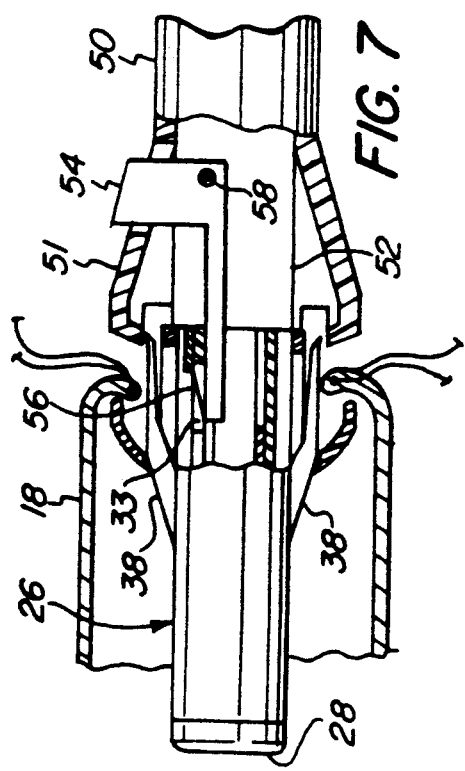
FIG. 7 is a side elevational view, partly in cross-section, showing the distal adapter and a handle assembly in accordance with the present invention.

FIG. 7 shows a disposable handle 50 used to insert the distal adapter within the open end of the upper bowel section. The handle and distal adapter are normally inserted through an abdominal incision in the patient.

The handle has a flared end 51 and includes a central shaft 52 for abutting the distal sleeve and a latch 54 for connecting the handle with the distal adapter. The latch includes an angled catch 56 at its distal end to engage with opening 33 in the distal sleeve.

In use, the distal adapter with the unitary member mounted thereon and the handle connected thereto is inserted through an abdominal incision in the patient and into the open end of the upper bowel. A purse-string suture 57 is applied to the open end and then suture is drawn to gather the open end around fingers 38 as shown in FIG. 2. The open end of the bowel is closed around the alignment fingers 38 and not the neck of the unitary member. A gap should remain between the sutured bowel end and the neck so the unitary member on the distal adapter can receive the unitary member on the proximal adapter. Once the purse string gathers the open end around the alignment fingers, the holder is disconnected from the distal adapter by urging latch 54 downward to rotate about pin 58 and disengage the catch 56 from the opening 33 in the plastic sleeve. The holder is removed from the patient through the incision in the abdomen and can be discarded.

The proximal adapter 14 will be discussed in detail with reference to FIGS. 4 through 6 and 9. The proximal adapter comprises a stepped proximal sleeve 60 having a main section 62 with a first diameter and a stepped section 64 with a reduced diameter. The stepped section includes a latch 66 biased outwardly by spring 68. The latch fits into an opening in the applicator in a manner that will be discussed in detail below. An angled surface at the open end of the proximal sleeve forms a shoulder 69 against which the head of the unitary member rests when it is mounted on the proximal adapter.

Coaxially mounted within the sleeve is a tubular proximal spool 70. The spool is biased in a distal, or second, direction by a spring 72 toward the open end of the sleeve and includes an outer lip 74 at its distal end. Coaxiallymmounted around the spool is a proximal four-fingered gripper 76 and diametrically opposed alignment fingers 78. The alignment fingers are connected to the spool by one or more screws 80 and therefore slide axially with the spool. The gripper comprises an annular ring 82 mounted around the spool and four radially spaced fingers 84 that can extend through the open end of the sleeve. Each finger has an upturned ridge 86 for engaging a ridge 27 on the head of the unitary member when it is mounted on the proximal adapter. The gripper also includes a limit pin 88 extending through an elongated slot 61 in the sleeve 60 in a direction perpendicular to the axial direction of the sleeve. Axial movement of the proximal gripper is limited by movement of the pin within the elongated slot.

The proximal adapter is connected to a distal end of the applicator 16 as shown in FIG. 1. Specifically, the applicator includes an elongated tube 90 with a handle assembly 92 connected to its proximal end and a collar 94 connected to its distal end. The tube can be curved as shown in FIG. 1 to assist its entry into the anal orifice and through the rectum of the patient. The proximal adapter is connected to the applicator by engaging the latch 66 in an opening 96 in the collar as shown in FIG. 4.

Figure 11:
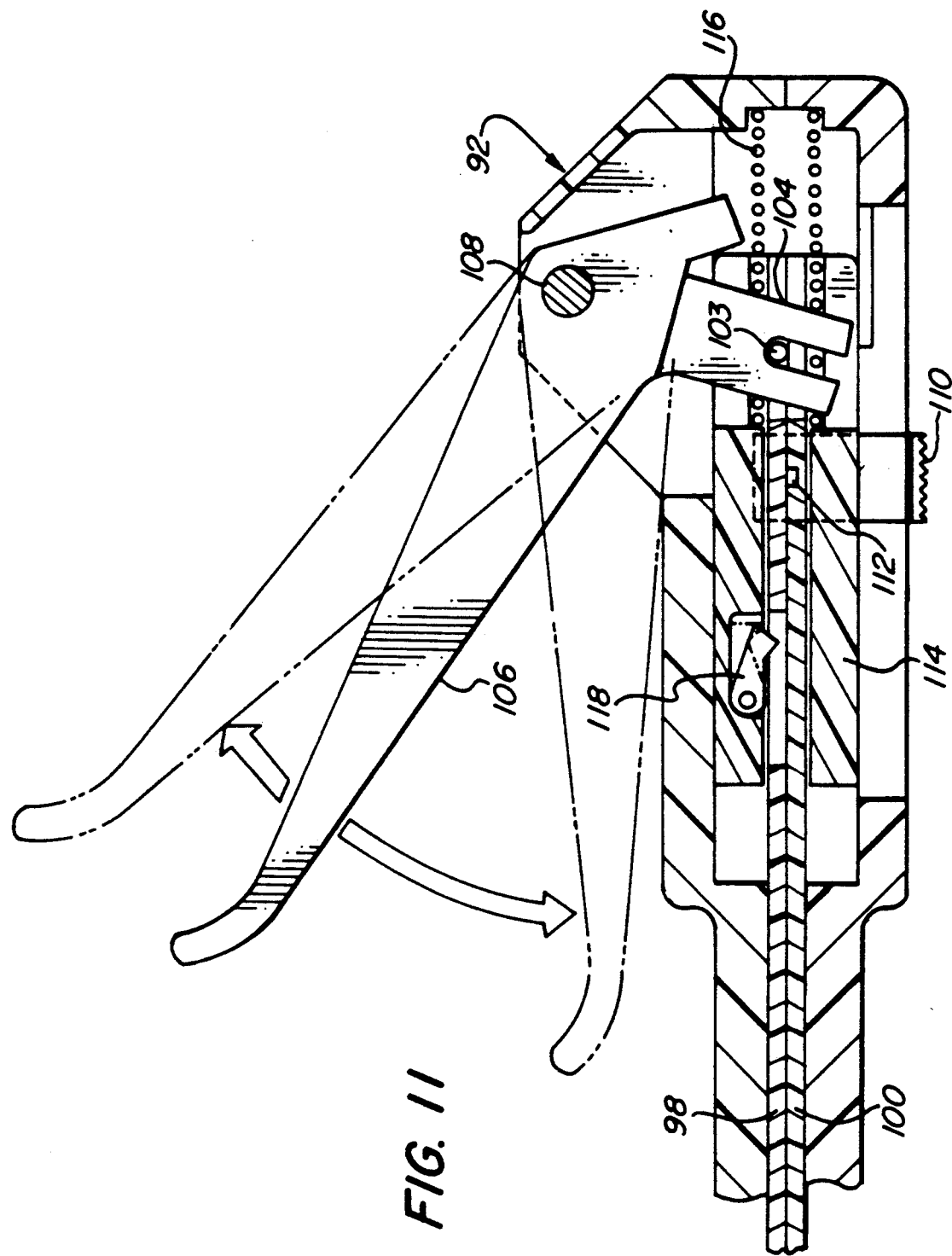
FIG. 11 is a cross-sectional view of a handle assembly of the applicator in accordance with the present invention.
Figure 12:
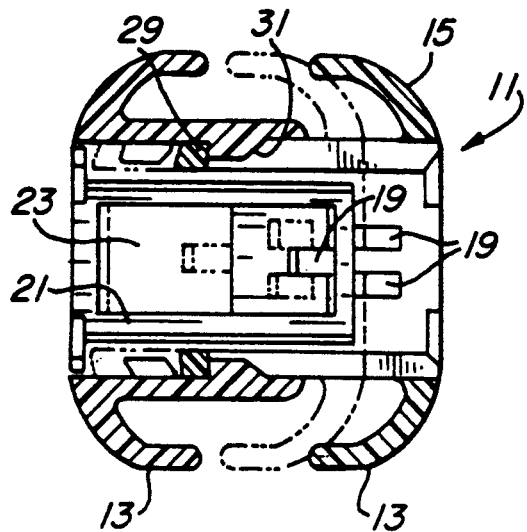
FIG. 12 is a cross-sectional side view of an anastomosis ring.
Figure 13:
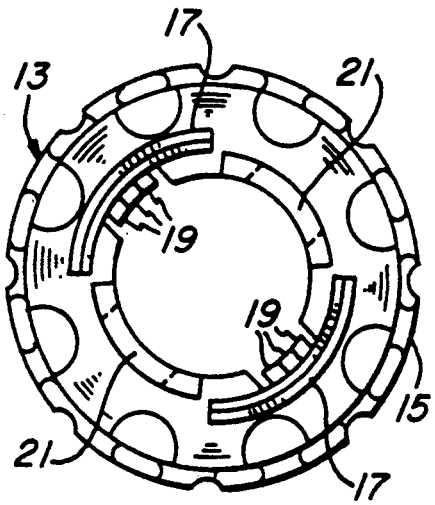
FIG. 13 is a bottom plan view of a unitary member of an anastomosis ring.
Figure 14:
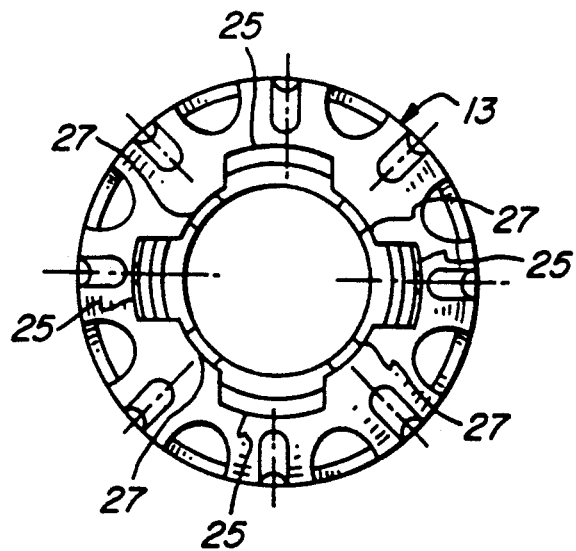
FIG. 14 is a top plan view of a unitary member of the anastomosis ring.

Upper and lower rods 98 and 100, respectively, extend axially through the applicator and engage with the distal applicator. The rods are preferably made of a flexible material so they can easily slide through the curved tube 90. The rods are connected at their proximal ends to the handle assembly as shown in FIG. 11. Upper rod 98 has a pin 103 engaged with a slotted end 104 of closing actuator, or trigger lever, 106. The closing actuator pivots about pivot pin 108 in the handle assembly and is actuated to slide the upper rod back and forth. The lower rod is connected to course actuator, or knob, 110 by connector 112. The course actuator extends through the bottom of the handle assembly and slides back and forth to control the lower rod. Within the handle assembly itself is a sliding collar 114 biased toward the distal end of the applicator by spring 116. The sliding collar includes a spring-loaded catch 118 for engaging a notch in the upper rod when the upper rod is pulled all the way back (toward the proximal end of the applicator).

The distal tip ends of the rods can be seen in FIG. 9. Upper rod 98 has a first spring-loaded catch 120 for capturing the distal adapter and a second spring-loaded catch 122 for engaging the spool 70 in the proximal adapter. The lower rod is longer than the upper rod and includes at its distal tip a contact pin 102 extending upwardly. In this manner, when the lower rod is pulled rearwardly in the first direction, i.e. toward the proximal end, the contact pin will abut the tip end of the upper rod to also pull it rearwardly. However, when the lower rod is pushed forwardly in the second direction, i.e. toward the distal end, the contact pin does not carry forward the upper rod. Rather it is locked in a rearward position by the catch 118 as depicted in FIG. 11.

A unitary member is mounted on the proximal adapter in substantially the same way as it is mounted on the distal adapter. That is, with the proximal spool 70 biased rearwardly to permit the fingers 84 of the gripper to flex radially inwardly, the head of the unitary member is slipped over the proximal adapter and the alignment fingers are inserted through two diametrically opposed notches in the unitary member. The gripper is then slid in the second direction until the fingers extend past the ridges 27 in the unitary member and flex radially outwardly in their naturally biased position. In the mounted position, the head of the unitary member comes to rest against the shoulder 69 of the sleeve and the ridges 86 of each finger on the gripper engage an underside of a ridge on the unitary member. The rearward force on the spool 70 is released and it extends forwardly by the biasing force of spring 72. This position places the outer lip 74 of the spool against the distal ends of the fingers 84, thus preventing them from flexing radially inwardly and securing the unitary member in the proximal adapter.

Figure 8:
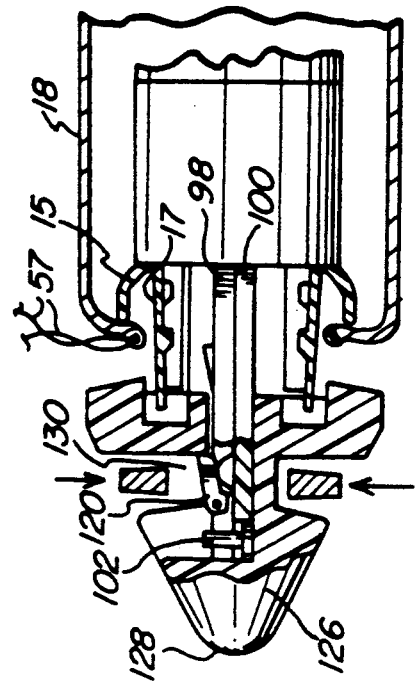
FIG. 8 is a side elevational view, partly in cross-section, showing the proximal adapter and a blunt cap in accordance with the present invention.

FIG. 8 shows a blunt cap 126 that is connected to the distal end of the actuator to guide the proximal adapter through the lower bowel. The blunt cap has a rounded nose 128 to make entry of the applicator and proximal adapter through the anal orifice of the patient easier and less painful. The rounded nose also protects the fragile rectal walls of the patient and the thin neck of the unitary member. The blunt cap includes a notched opening 130 through which the first catch 120 of the upper rod extends to secure the blunt cap on the applicator. In this regard, the applicator, the proximal adapter with a unitary member mounted thereon and the blunt cap can all be packaged as a single pre-assembled proximal applicator unit ready for transanal insertion into the patient. Likewise, the distal adapter with a mounted unitary member and handle can also be packaged as a pre-assembled distal applicator unit.

In operation, the distal applicator unit is inserted through an abdominal incision and into an open end of the upper bowel in the manner discussed above. After the purse-string suture is drawn snugly (not tightly) around the distal alignment fingers, the handle is released from the distal adapter and withdrawn through the incision.

The proximal applicator unit is then inserted through the anal orifice in the patient until the blunt cap exits through the open end of the lower bowel. The blunt cap is then disengaged by depressing the first catch 120 on the upper rod, removed through the abdominal incision and discarded.

With the unitary member 13', loosely positioned in the open end of the lower bowel, a frangible safety latch 111 on the handle assembly is broken and the trigger lever is pulled upwardly as shown in FIG. 1 to push the upper rod forward into the distal adapter. The lower rod also travels forward as the contact pin 102 is pushed by the distal tip of the upper rod. The first catch 120 on the upper rod engages the opening 33 in the distal sleeve to connect the distal adapter and the actuator. The course actuator is then slid rearwardly to pull the lower rod, and with it the upper rod and distal adapter, closer to the proximal adapter. A purse-string suture is made in the open end of the lower bowel and tightened to draw the open end snugly around proximal alignment fingers 78. FIG. 2 shows the drawn purse string sutures 57 at this point in the surgical procedure. As will be appreciated, the proximal alignment fingers 78 are offset 90° from the distal alignment fingers 38. The trigger lever is then pushed downwardly to further retract the upper rod and distal adapter and draw the unitary members closer together until they are interlocked in a closed position. A window 113 in the handle assembly enables the surgeon-user to see indicia on the upper rod to indicate its fully retracted position.

With the open ends of the bowel clamped between the closed anastomosis ring as shown in FIG. 3, the distal and proximal adapters are withdrawn from the body in the following manner. As the upper rod is being fully retracted by actuation of the trigger lever, second catch 122 abuts proximal spool 70 in the proximal adapter as shown in FIG. 4 and pushes it rearwardly against the bias of spring 72. Moving rearwardly with the proximal spool are alignment fingers 78 to release their position within the notches in the unitary member. The rearward movement of the proximal spool also pushes the four-fingered proximal gripper rearwardly as the outer lip 74 engages the annular ring 82 as shown in FIG. 6. As the gripper is pushed rearwardly the gripper fingers are biased radially inwardly and retracted within the sleeve to release their grip on the unitary member. The spring-loaded catch 118 in the handle assembly extends in a slot in the upper rod when it is fully retracted to prevent the upper rod from moving in the second direction. To release the distal adapter, the course actuator is pushed forwardly to force lower rod 100 into the distal tubular spool as shown in FIG. 4. The tubular spool is pushed forwardly against the bias of spring 36 to place a reduced diameter section 35 of the distal spool opposite to the retaining fingers 45 on retaining sleeve 44 (see FIG. 5). Instead of having a reduced diameter section, the distal spool could provide slots or openings to allow the retaining fingers to flex radially inwardly. Forward movement of the distal spool also permits the alignment fingers to flex radially inwardly as discussed above. The retracted alignment fingers collapse within the plastic sleeve as shown in FIG. 4, allowing the distal adapter to be withdrawn axially through the center of the anastomosis ring.

Figure 5:
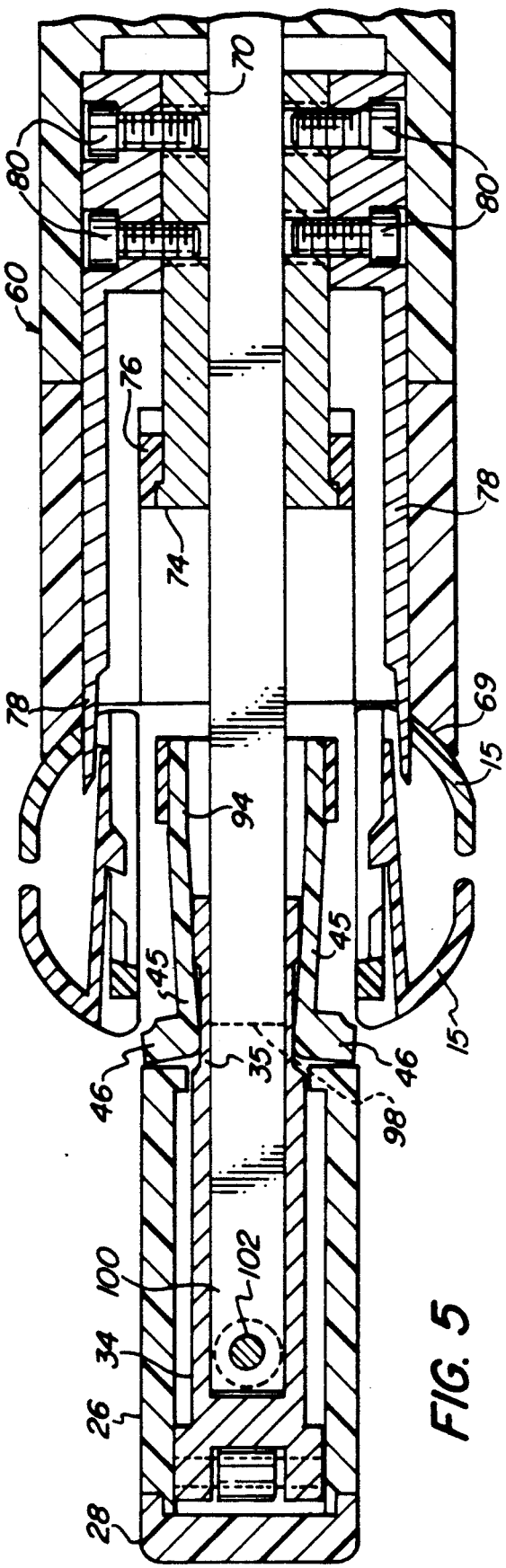

The retaining fingers can now flex radially inwardly as shown in FIG. 5 as the distal adapter is withdrawn and the projections 46 slide off the ridges of the head member Therefore, the applicator with the distal and proximal adapter attached can be withdrawn transanally. With the insertion device withdrawn, the abutting ends of the bowel clamped between the anastomosis ring can heal and naturally grow together.

Although specific embodiments of the present invention have been described above in detail, it will be understood that this description is merely for purposes of illustration. Various modifications of and equialent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

We claim:

1. A surgical device for inserting an anastomosis ring, having first and second separable unitary members formed to interlock, together, into upper open and lower open ends of a tubular anatomic member and for closing said first and said second unitary members together to join said upper and loer ends; said surgical device comprising:

distal adapter means configured for temporarily mounting a first unitary member so that said first unitary member can be secured within said upper open end of said anatomotic member, said distal adaptor means including a hollow distal sleeve and first alignment means for aligning the first unitary member on said distal sleeve, said first alignment means being axially movable within said distal sleeve and biased in a first direction;

proximal adaptor means configured for temporarily mounting a second unitary member so that said second unitary member can be secured within said lower open end of the anatomic member, said distal adaptor means being separable and independently manipulable from said proximal adaptor means; and actuating means, connected to said proximal adaptor means, for engaging said distal adaptor means and for drawing it relative to said proximal adaptor means thereby to interlock said first unitary member temporarily mounted on said distal means and said second unitary member temporarily mounted on said proximal adaptor means and for releasing said distal adaptor means from said first unitary member and said proximal adaptor means from said second unitary member.

2. A surgical device according to claim 2, said distal adapter means further including distal securing means for securing the first unitary member on said distal sleeve, said securing means including a gripper mounted with said distal sleeve and biased radially outwardly and a retainer mounted on said distal sleeve, with said retainer being flexible radially inwardly when said first alignemnt means is biased in a second direction within said distal sleeve.

3. A surgical device according to claim 2, said proximal adapter means including a hollow proximal sleeve and second alignment means for aligning the second unitary member on said proximal sleeve, said second alignment means being axially movable within said proximal sleeve and biased in the second direction.

4. A surgical device according to claim 3, said proximal adapter means further including proximal securing means, cooperating with said second alignment means, for securing the second unitary member.

5. A surgical device according to claim 4, said actuating means including an elongated housing, manipulating means engagable with said distal adapter means and said proximal adapter means and disposed within said housing for manipulating said distal adapter means and said proximal adapter means, and a handle assembly connected to said housing for operating said manipulating means.

6. a surgical device according to claim 5, further comprising handle means, connectable to said distal adapter means, for inserting said distal adapter means and mounted unitary member within the upper open end of the anatomic member.

7. A surgical applicator for inserting an anastomosis ring having first and second unitary members into separated upper open and lower open ends of a tubular anatomic member and for closing said first and second unitary members together to join said separated upper and lower ends; said surgical applicator comprising:

distal applicator means for positioning a first unitary member in said upper open end of said tubular anatomic member, said distal applicator means having a distal adapter, configured to mount said first unitary member, and a distal adapter holder removably connected to said distal adapter for together therewith inserting said idstal adapter and said first unitary member into said upper open end; and proximal applicator means for positioning a second unitary member in said lower open end of said tubular anatomic member, said proximal applicator means including a proximal adapter configured to mount said second unitary member, and actuating means, connected to said proximal adapter, for engaging said distal adapter after said distal adapter holder is removed therefrom and for drawing said distal adapter relative to said proximal adapter thereby to interlock said first unitary member mounted on said distal adapter and said second unitary member mounted on said proximal adapter and for releasing said distal adapter from said first unitary member and said proximal adapter from said second unitary member.

8. A surgical applicator according to claim 7, said distal adapter including a hollow distal sleeve and first alignment means for aligning the first unitary member on said distal sleeve, said first aligning means being axially movable within said distal sleeve.

9. A surgical applicator according to claim 8, said first alignment means including a distal spool and a distal spring for biasing said distal spool in a first direction within said distal sleeve, and further including distal alignment fingers pivotably supported on said distal spool and extending through elongated grooves in said distal sleeve for aligning the first unitary member.

10. A surgical applicator according to claim 8, wherein said actuating means includes means for biasing said alignment fingers radially inwardly by biasing said distal spool in a second direction within said distal sleeve.

11. A surgical applicator according to claim 10, said distal adapter further including distal securing means for securing the first unitary member on said distal sleeve.

12. A surgical applicator according to claim 11, said distal securing means including a distal gripper and a retainer mounted on said distal sleeve, said gripper being biased radially outwardly and, when said spool is biased in the second direction within said distal sleeve, said retainer being flexible radially inwardly.

13. A surgical applicator according to claim 12, said distal gripper including a plurality of flexible fingers engaging the first unitary member and preventing axial movement of the first unitary member in the first direction.

14. A surgical applicator according to claim 13, said retainer including a plurality of fingers engaging the first unitary member and preventing axial movement of the first unitary member in the second direction.

15. A surgical applicator according to claim 14, said proximal adapter including a hollow proximal sleeve and second alignment means for aligning the second unitary member on said proximal sleeve, said second alignment means being axially movable within said proximal sleeve.

16. A surgical applicator according to claim 15, said second aligning means including a proximal spool and a proximal spring for biasing said proximal spool in the second direction within said proximal sleeve, and further including proximal alignment fingers supported on said proximal spool for aligning the second unitary member.

17. A surgical applicator according to claim 16, said proximal adapter further including proximal securing means supported on said proximal spool and cooperating therewith for securing the second unitary member on said proximal sleeve.

18. A surgical applicator according to claim 17, wherein said actuating means includes means for biasing said proximal securing means radially inwardly by biasing said proximal spool in the first direction.

19. A surgical applicator according to claim 18, wherein said proximal securing means includes a gripper having a plurality of fingers for engaging the second unitary member.

20. A surgical applicator according to claim 19, said actuating means including an elongated housing, manipulating means disposed within said housing for manipulating said distal and proximal adapters and a handle assembly connected to said housing for operating said manipulating means.

21. A surgical applicator according to claim 20, said actuating means further including collar means mounted on said housing for connecting said actuating means to said proximal adapter.

22. A surgical applicator according to claim 21, said manipulating means including first and second rods disposed within said housing for movement relative to each other, with said first rod having a first catch for engaging said distal adapter and a second catch for biasing said proximal spool in the first direction, and said second rod having a contact pin for driving said first rod in the first direction and an abutting end for biasing said distal spool in the second direction.

23. A surgical applicator according to claim 22, wherein said handle assembly includes a pivoting trigger for actuating said first rod and a sliding knob for actuating said second rod.

24. A surgical applicator according to claim 23, said handle assembly including a third catch for engaging said first rod when it is retracted in the first direction by said trigger.

25. A surgical applicator according to claim 24, said distal adapter holder including a pivotably mounted latch connectable to said distal sleeve.

26. A surgical applicator according to claim 25, further comprising a cap connectable to a distal end of said actuating means for guiding said proximal adapter means and a proximal member mounted thereon through an anal opening.

27. A surgical applicator according to claim 26, wherein said cap has a rounded nose and an opening for receiving said first catch on said first control rod.

28. A transanal insertion device for surgically inserting an anastomosis ring having two unitary members into a tubular anatomic member, comprising:
 a distal adapter having a hollow distal sleeve, a spring-loaded spool axially movable with said distal sleeve, a distal spring for biasing said distal spool in a first direction, and distal alignment fingers pivotably connected to said distal spool for aligning a first unitary member, said distal adapter also including a distal gripper secured on said distal sleeve and a retaining sleeve for securing the first unitary member thereon;
 a proximal adapter having a hollow proximal sleeve, a spring-loaded proximal spool axially movable within said proximal sleeve, a proximal spring biasing said proximal spool in a second direction, and proximal alignment fingers connected to said proximal spool for aligning the second unitary member, said proximal adapter also including a proximal gripper secured on said proximal sleeve for securing the second unitary member thereon; and
 an actuator connecting to said proximal adapter and having an elongated tube with a collar connected to a distal end, a handle assembly connected to a proximal end, and first and second flexible rods connected to said handle assembly and extending through said elongated tube.

29. A transanal insertion device according to claim 28, said distal sleeve including a first section of a first diameter and a second section of a second diameter smaller than the first diameter, said first section including a plurality of elongated slots through two of which extend said distal alignment fingers and said second section including an engaging opening.

30. A transanal insertion device according to claim 29, further comprising biasing means for biasing said distal alignment fingers radially inwardly when said distal spool is biased in the second direction.

31. A transanal insertion device according to claim 30, said biasing means including complimentary cam surfaces on said distal alignment fingers and said first section of said distal sleeve for biasing said alignment fingers radially inwardly.

32. A transanal insertion device according to claim 31, said retaining sleeve including a plurality of retaining fingers for engaging the first unitary member.

33. A transanal insertion device according to claim 32, said distal spool including spacing means for allowing said retaining fingers to be biased radially inwardly when said distal spool is biased in the second direction.

34. A transanal insertion device according to claim 33, said spacing means including a plurality of openings in said distal spool for receiving said retaining fingers when said distal spool is biased in the second direction.

35. A transanal insertion device according to claim 34, said spacing means including a reduced diameter section on said distal spool disposed opposite to said retaining fingers when said distal spool is biased in the second direction.

36. A transanal insertion device according to claim 35, wherein said retaining sleeve is coaxially disposed on said second section of said distal sleeve.

37. A transanal insertion device according to claim 36, said distal gripper including a plurality of gripping fingers biased radially outwardly.

38. A transanal insertion device according to claim 37, wherein said distal gripper is coaxially disposed on said second section of said distal sleeve.

39. A transanal insertion device according to claim 38, said proximal gripper including a gripping collar coaxially disposed around said proximal spool and having a plurality of proximal gripping fingers each with an outer ridge, and said proximal spool having an outer lip for engaging said gripping collar, wherein said proximal gripping fingers can flex radially inwardly when said outer lip engages said gripping collar.

40. A transanal insertion device according to claim 39, wherein said proximal gripper also includes a transverse limit pin extending through said proximal sleeve for limiting axial movement of said proximal gripper.

41. A transanal insertion device according to claim 40, wherein said proximal sleeve includes a reduced diameter section to be received in said collar of said actuator.

42. A transanal insertion device according to claim 41, wherein said first flexible rod includes a first catch for engaging the engaging opening in said second section of said distal sleeve and a second catch for abutting said proximal spool and driving it in the first direction.

43. A transanal insertion device according to claim 42, wherein said second flexible rod includes an abutting end for driving said distal spool in the second direction and a contact pin for driving said first flexible rod in the first direction.

44. A transanal insertion device according to claim 43, further comprising a trigger pivotably disposed on said handle assembly and connected to said first flexible rod.

45. A transanal insertion device according to claim 44, further comprising a safety latch connected between said trigger and said handle assembly.

46. A transanal insertion device according to claim 45, further comprising indicating means on said handle assembly for indicating when said first flexible rod is fully retracted in the first direction.

47. A transanal insertion device according to claim 46, wherein said elongated tube is curved.

48. A transanal insertion device according to claim 47, further comprising a knob disposed for sliding movement within said handle assembly and connected to said second flexible rod.

49. A transanal insertion device according to claim 46, further comprising a sliding collar disposed for axial movement within said handle assembly and a spring for biasing said sliding collar in the second direction, wherein said sliding collar slides relative to said first and second flexible rods within said handle assembly.

50. A transanal insertion device according to claim 49, further comprising handle means, connectable to said distal adapter, for inserting said distal adapter and first unitary member within the upper open end of the anatomic member.

51. A transanal insertion device according to claim 50, wherein said handle means includes a pivotably mounted latch connectable to said distal sleeve.

52. A transanal insertion device according to claim 51, further comprising a cap connectable to said actuator for guiding said proximal adapter and second unitary member through an anal opening orifice in the patient.

53. A transanal insertion device according to claim 52, wherein said cap has a rounded nose and an opening for receiving said first catch on said first flexible control rod.

54. A transanal insertion device according to claim 53, wherein said handle assembly includes restriction means for engaging said first flexible rod when it is retracted in the first direction and preventing it from being actuated in the second direction.

55. A method for surgically anastomosing separated upper open and lower open ends of a tubular anatomic member, which is in communication with a natural body orifice, with an anastomosis ring having first and second mating unitary members, said method comprising the steps of:

providing a distal adapter for mounting the first unitary member, a separable proximal adapter for mounting the secondary unitary member, and an actuator connected to said proximal adapter for mating the first and second unitary members together;

inserting the distal adapter and a first unitary member mounted thereon through a bodily incision into the upper open end of the tubular member;

inserting the actuator connected to the proximal adapter and a second unitary member mounted on the proximal adapter into the lower open end tubular member through the natural body orifice;

engaging the distal adapter with the actuator;

drawing the distal adapter and proximal adapter together with the actuator to mate the first and second unitary members together;

releasing the distal adapter from the first unitary member and releasing the proximal adapter from the second unitary member; and withdrawing the distal adapter, the proximal adapter, and the actuator from the anatomic member through the natural body orifice.

56. A method according to claim 55, wherein the step of releasing the distal adapter and the proximal adapter further includes the step of utilizing the actuator to release the distal adapter from the first unitary member and the proximal adapter from the second unitary member.

* * * * *